(12) United States Patent
Yamaura et al.

(10) Patent No.: US 11,624,049 B2
(45) Date of Patent: Apr. 11, 2023

(54) CELL CULTURING APPARATUS, CULTURE SOLUTION ASPIRATOR, AND CELL CULTURING METHOD

(71) Applicant: Orizuru Therapeutics, Inc., Kangawa (JP)

(72) Inventors: Junji Yamaura, Kanagawa (JP); Shinobu Kuwae, Kanagawa (JP); Taro Toyoda, Kyoto (JP); Shuhei Konagaya, Kyoto (JP)

(73) Assignee: Orizuru Therapeutics, Inc., Kanagawa (JP)

( * ) Notice: Subject to any disclaimer, the term of this patent is extended or adjusted under 35 U.S.C. 154(b) by 54 days.

(21) Appl. No.: 16/954,889

(22) PCT Filed: Dec. 21, 2018

(86) PCT No.: PCT/JP2018/047200
§ 371 (c)(1),
(2) Date: Jun. 17, 2020

(87) PCT Pub. No.: WO2019/124540
PCT Pub. Date: Jun. 27, 2019

(65) Prior Publication Data
US 2020/0392445 A1 Dec. 17, 2020

(30) Foreign Application Priority Data
Dec. 22, 2017 (JP) .............................. JP2017-245751

(51) Int. Cl.
*C12M 1/26* (2006.01)
*C12M 1/06* (2006.01)
*C12M 1/00* (2006.01)

(52) U.S. Cl.
CPC ............ *C12M 33/04* (2013.01); *C12M 27/02* (2013.01); *C12M 29/04* (2013.01)

(58) Field of Classification Search
CPC ....... C12M 33/04; C12M 27/02; C12M 29/04
(Continued)

(56) References Cited

U.S. PATENT DOCUMENTS

2015/0118745 A1   4/2015  Iwamoto et al.
2016/0355774 A1*  12/2016 Konishi ................. C12M 23/38

FOREIGN PATENT DOCUMENTS

CN          201334538 Y      11/2009
CN          102337212 B       9/2013
(Continued)

OTHER PUBLICATIONS

Supplementary European Search Report dated Aug. 26, 2021 in EP 18893169.5.
(Continued)

*Primary Examiner* — Michael L Hobbs
*Assistant Examiner* — Lenora A Abel
(74) *Attorney, Agent, or Firm* — Foley & Lardner LLP

(57) ABSTRACT

Provided is a cell suspension culturing apparatus suitable for large-scale culture of cells, the cell culturing apparatus comprising a culture solution aspirator having a double-tube structure comprising an outer tube and an inner tube inserted in a lumen of the outer tube, and a suspension culture vessel, wherein in the culture solution aspirator, the outer tube comprises a filter through which a culture solution is passed, the inner tube comprises a suction port for the culture solution passed through the filter, and an air hole which communicates the lumen of the outer tube with the outside is disposed distally in a direction of insertion of the outer tube into the suspension culture vessel.

5 Claims, 10 Drawing Sheets

(58) Field of Classification Search
USPC .................................................... 435/297.1
See application file for complete search history.

(56) References Cited

FOREIGN PATENT DOCUMENTS

| CN | 103031247 B | 2/2016 |
| EP | 0 529 089 A1 | 3/1993 |
| TW | 238851 B | 9/2005 |
| WO | WO 2013/161885 A1 | 10/2013 |
| WO | WO 2015/122528 A1 | 8/2015 |
| WO | WO 2017/110004 A1 | 6/2017 |

OTHER PUBLICATIONS

International Search Report dated Mar. 19, 2019, in PCT/JP2018/047200.
Olmer et al., "Suspension Culture of Human Pluripotent Stem Cells in Controlled, Stirred Bioreactors," Tissue Engineering: Part C, May 22, 2012, 18(10):772-784.
Office Action dated Feb. 13, 2023 in TW 107146514.

\* cited by examiner

CELL CULTURING APPARATUS, CULTURE SOLUTION ASPIRATOR, AND CELL CULTURING METHOD

TECHNICAL FIELD

The present invention relates to a cell culturing apparatus, a culture solution aspirator and a cell culturing method.

BACKGROUND ART

The clinical application of regenerative medicine using pluripotent stem cells such as embryonic stem cells (ES cells) and induced pluripotent stem cells (iPS cells) requires developing a culturing apparatus capable of quantitatively expanding (scaling up) a laboratory culturing approach using dishes or flasks, and producing cells with quality above a certain level in a large amount and at a low cost. Efficient oxygen supply or culture solution replacement is important for the establishment of a process of large-scale culture of cells, and low cost mediated by reduction in the amount of growth factors used, etc. is also demanded therefor.

Cell culturing methods include adherent culture which involves culturing cells attached to an incubator surface coated with an extracellular matrix or feeder cells, and suspension culture (or floating culture) which involves culturing cells floating in a culture solution. The maximum yield of cells in the adherent culture depends on a culture area, whereas the maximum yield of cells in the suspension culture depends on a culture solution volume. Hence, the suspension culture is advantageous for scaling up.

Cells such as pluripotent stem cells form aggregates when suspension-cultured. Non Patent Literature 1 discloses a technique of allowing pluripotent stem cells to proliferate stably by stirring a culture solution so as not to cause cell death through shear stress ascribable to culture solution flow, while suppressing the excessive aggregation of cells using a spinner flask.

CITATION LIST

Non Patent Literature

Non Patent Literature 1: Olmer R, et al., "Suspension culture of human pluripotent stem cells in controlled, stirred bioreactors.", Tissue Eng. Part. C Methods, 2012, 18 (10): 772-84

SUMMARY OF INVENTION

Technical Problem

Culture solution replacement in a laboratory culturing approach can be performed by separating cells from the culture solution by centrifugation or the like, and resuspending the separated cells in a fresh culture solution. However, large-scale culture based on suspension culture involves the difficulty of carrying out a cell separation operation such as centrifugation. Therefore, the culture solution is replaced by separating the cells from the culture solution by the spontaneous precipitation of aggregates of the cells. This replacement of the culture solution requires time to temporarily stop the stirring of the culture solution and wait for the spontaneous precipitation of cells. Therefore, this approach requires time and effort and might cause unstable and inhomogeneous proliferation or properties of cells in that time.

A principal object of the present invention is to provide a cell suspension culturing apparatus suitable for large-scale culture of cells.

Solution to Problem

In order to attain the object, the present invention provides the following [1] to [4h]:

[1] A cell culturing apparatus comprising a culture solution aspirator having a double-tube structure comprising an outer tube and an inner tube inserted in a lumen of the outer tube, and a suspension culture vessel,
wherein
in the culture solution aspirator,
the outer tube comprises a filter through which a culture solution is passed,
the inner tube comprises a suction port for the culture solution passed through the filter, and
an air hole which communicates the lumen of the outer tube with the outside is disposed distally in a direction of insertion of the outer tube into the suspension culture vessel.

[1a] The cell culturing apparatus according to [1], wherein when the culture solution aspirator is placed such that the filter is positioned in a lower portion thereof, the air hole is disposed above the suction port.

[1b] The cell culturing apparatus according to [1] or [1a], wherein the inner tube is configured such that a front end in a direction of insertion into the suspension culture vessel serves as the suction port, and a tube port at the opposite end is connected to a pump.

[1c] The cell culturing apparatus according to [1b], wherein the outer tube comprises the filter at the front end in the direction of insertion into the suspension culture vessel, and is configured such that the opposite end serves as an insertion port for the inner tube, wherein the insertion port is configured such that a gap between the lumen surface of the outer tube and the outer surface of the inner tube serves as the air hole.

[1d] The cell culturing apparatus according to [1b], wherein the outer tube comprises the filter at the outer periphery.

[2] The cell culturing apparatus according to any of [1] and [1a] to [1d], further comprising a culture solution supply channel which supplies a culture solution to the suspension culture vessel.

[2a] The cell culturing apparatus according to any of [1], [1a] to [1d], and [2], wherein the suspension culture vessel comprises a stirrer for stirring a culture solution.

[2b] The cell culturing apparatus according to [2a], wherein the cell culturing apparatus is configured such that the stirrer is actuated upon actuation of the culture solution aspirator.

[3] A culture solution aspirator having a double-tube structure comprising an outer tube and an inner tube inserted in a lumen of the outer tube, wherein
the outer tube comprises a filter through which a culture solution is passed,
the inner tube comprises a suction port for the culture solution passed through the filter, and
an air hole which communicates the lumen of the outer tube with the outside is disposed distally in a direction of insertion of the outer tube into the culture solution.

[3a] The culture solution aspirator according to [3], wherein the inner tube is configured such that a front end in the direction of insertion into the culture solution serves as the suction port, and a tube port at the opposite end is connected to a pump.

[3b] The culture solution aspirator according to [3a], wherein
the outer tube comprises the filter at the front end in the direction of insertion into the culture solution, and is configured such that the opposite end serves as an insertion port for the inner tube, wherein
the insertion port is configured such that a gap between the lumen surface of the outer tube and the outer surface of the inner tube serves as the air hole.

[3c] The culture solution aspirator according to [3a], wherein the outer tube comprises the filter at the outer periphery.

[3d] An outer tube constituting a culture solution aspirator according to any of [3] and [3a] to [3c], the outer tube being usable in combination with the inner tube.

[3e] An inner tube constituting a culture solution aspirator according to any of [3] and [3a] to [3c], the inner tube being usable in combination with the outer tube.

[4] A cell culturing method in a suspension culture vessel, comprising the step of
discharging a culture solution in the suspension culture vessel to the outside of the suspension culture vessel using a culture solution aspirator having a double-tube structure comprising an outer tube and an inner tube inserted in a lumen of the outer tube, wherein
in the culture solution aspirator,
the outer tube comprises a filter through which a culture solution is passed,
the inner tube comprises a suction port for the culture solution passed through the filter, and
an air hole which communicates the lumen of the outer tube with the outside is disposed distally in a direction of insertion of the outer tube into the suspension culture vessel.

[4a] The cell culturing method according to [4], wherein the step is performed concurrently with the supply of a culture solution to the suspension culture vessel.

[4b] The cell culturing method according to [4a], wherein in the step, the discharge is performed while a culture solution is supplied to the suspension culture vessel, thereby replacing the culture solution with the fresh one.

[4c] A cell culturing method in an airtight suspension culture vessel comprising a stirrer for a culture solution, comprising the step of
discharging a culture solution in the suspension culture vessel to the outside of the suspension culture vessel using a culture solution aspirator having a double-tube structure comprising an outer tube and an inner tube inserted in a lumen of the outer tube, wherein in the culture solution aspirator,
the outer tube comprises a filter through which a culture solution is passed,
the inner tube comprises a suction port for the culture solution passed through the filter, and
an air hole which communicates the lumen of the outer tube with the outside is disposed distally in a direction of insertion of the outer tube into the suspension culture vessel.

[4d] The cell culturing method according to [4c], wherein in the step, the actuation of the stirrer is maintained.

[4e] The cell culturing method according to [4d] or [4c], wherein the step is performed concurrently with the supply of a culture solution to the suspension culture vessel.

[4f] The cell culturing method according to [4e], wherein in the step, the discharge is performed while a culture solution is supplied to the suspension culture vessel, thereby replacing the culture solution with the fresh one.

[4g] A method for discharging or replacing a culture solution in a suspension culture vessel, comprising the step of discharging the culture solution in the suspension culture vessel to the outside of the suspension culture vessel using a culture solution aspirator having a double-tube structure comprising an outer tube and an inner tube inserted in a lumen of the outer tube, wherein in the culture solution aspirator,
the outer tube comprises a filter through which a culture solution is passed,
the inner tube comprises a suction port for the culture solution passed through the filter, and
an air hole which communicates the lumen of the outer tube with the outside is disposed distally in a direction of insertion of the outer tube into the suspension culture vessel.

[4h] A method for differentiating pluripotent or multipotent stem cells or pluripotent or multipotent stem cell-derived cells in a suspension culture vessel, comprising the step of discharging or replacing a culture solution in the suspension culture vessel, wherein
the step comprises discharging the culture solution in the suspension culture vessel to the outside of the suspension culture vessel using a culture solution aspirator having a double-tube structure comprising an outer tube and an inner tube inserted in a lumen of the outer tube, wherein
in the culture solution aspirator,
the outer tube comprises a filter through which a culture solution is passed,
the inner tube comprises a suction port for the culture solution passed through the filter, and
an air hole which communicates the lumen of the outer tube with the outside is disposed distally in a direction of insertion of the outer tube into the suspension culture vessel.

In order to attain the object, the present invention also provides the following [5] to [8]:

[5] A cell culturing apparatus comprising a suspension culture vessel and a culture solution aspirator, wherein the culture solution aspirator has a proximal end and a distal end, wherein
a tube port at the proximal end is configured to serve as a suction port for culture solution, and
a tube port at the distal end is connected to a pump; and
the suspension culture vessel comprises a stirrer for stirring a culture solution, and a filter through which a culture solution is passed, wherein
the filter divides the inside of the suspension culture vessel into a first region provided with the stirrer and a second region in which the culture solution aspirator is inserted.

[6] The cell culturing apparatus according to [5], wherein the filter is provided vertically or substantially vertically in the inside of the suspension culture vessel.

[7] The cell culturing apparatus according to [5] or [6], wherein the cell culturing apparatus is configured such that the stirrer is actuated upon actuation of the culture solution aspirator.

[8] The cell culturing apparatus according to any of [5] to [7], further comprising a culture solution supply channel which supplies a culture solution to the suspension culture vessel.

As used herein, "culture" or "culturing" means maintaining cells, sustaining the cells, and/or allowing the cells to proliferate and/or differentiate out of tissue or the body, for example, in a cell culture dish or a flask or in a culture vessel (tank). Preferably, "culture" or "culturing" means allowing cells to differentiate out of tissue or the body in a culture vessel (tank).

In another aspect, preferably, "culture" or "culturing" means maintaining cells or allowing the cells to proliferate out of tissue or the body in a culture vessel (tank).

As used herein, "pluripotency" means the ability to be able to differentiate into tissues and cells having various different shapes and functions and to be able to differentiate into cells of any lineage of the 3 germ layers. "Pluripotency" is different from "totipotency", which is the ability to be able to differentiate into any tissue of the living body, including the placenta, in that pluripotent cells cannot differentiate into the placenta and therefore, do not have the ability to form an individual.

As used herein, "multipotency" means the ability to be able to differentiate into plural and limited numbers of linages of cells. For example, mesenchymal stem cells, hematopoietic stem cells, neural stem cells are multipotent, but not pluripotent.

Advantageous Effects of Invention

The present invention provides a cell suspension culturing apparatus suitable for large-scale culture of cells.

DESCRIPTION OF EMBODIMENTS

Hereinafter, suitable modes for carrying out the present invention will be described with reference to the drawings. The embodiments described below are given merely for illustrating typical embodiments of the present invention. The scope of the present invention should not be interpreted as being limited by these embodiments.

[Cell Culturing Apparatus (First Aspect)]

The cell culturing apparatus according to the present invention comprises a culture solution aspirator having a double-tube structure comprising an outer tube and an inner tube inserted in the lumen of the outer tube, and a suspension culture vessel. In the culture solution aspirator, the outer tube comprises a filter through which a culture solution is passed. The inner tube comprises a suction port for the culture solution passed through the filter. An air hole which communicates the lumen of the outer tube with the outside is disposed distally in the direction of insertion of the outer tube into the suspension culture vessel. In this context, the "outside of the outer tube" may correspond to a vapor phase in the culture vessel when the culture solution aspirator is inserted in the suspension culture vessel.

Figure 1:
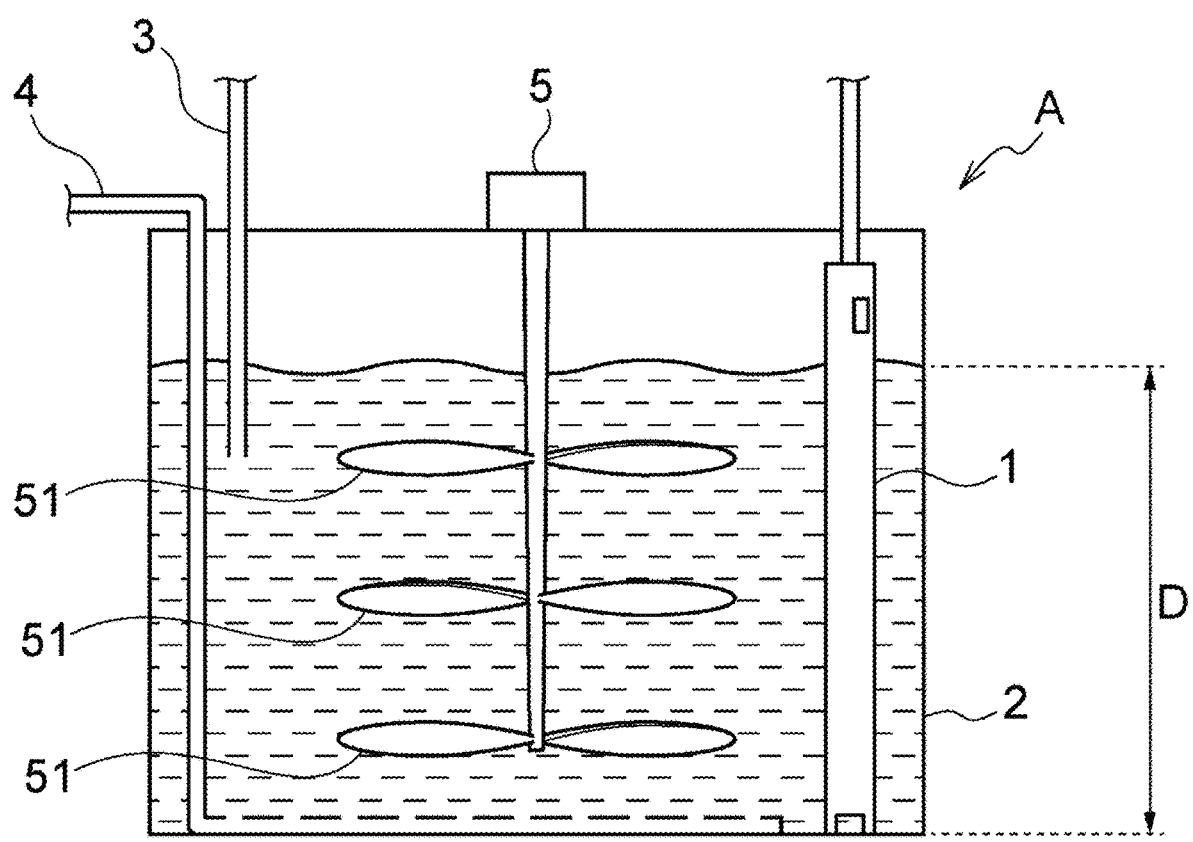
FIG. 1 is a diagram illustrating the configuration of the cell culturing apparatus according to the present invention.

FIG. 1 shows the configuration of the cell culturing apparatus according to the present invention. Cell culturing apparatus A comprises culture solution aspirator 1 according to the first embodiment of the present invention, and airtight suspension culture vessel 2 which retains cells and a culture solution. The culture solution aspirator 1 functions to discharge the culture solution in the suspension culture vessel 2 to the outside. In the drawing, reference numeral 3 denotes a culture solution supply channel, and reference numeral 4 denotes an air supply channel. The culture solution supply channel 3 functions to supply a culture solution into the suspension culture vessel 2. The air supply channel 4 functions to supply air into the suspension culture vessel 2. Reference numeral 5 denotes a stirrer comprising stirring bar 51. The stirrer 5 stirs the culture solution in the suspension culture vessel 2 by rotating or moving up and down the stirring bar 51. The culture solution aspirator 1 may function as the culture solution supply channel.

Figure 2:
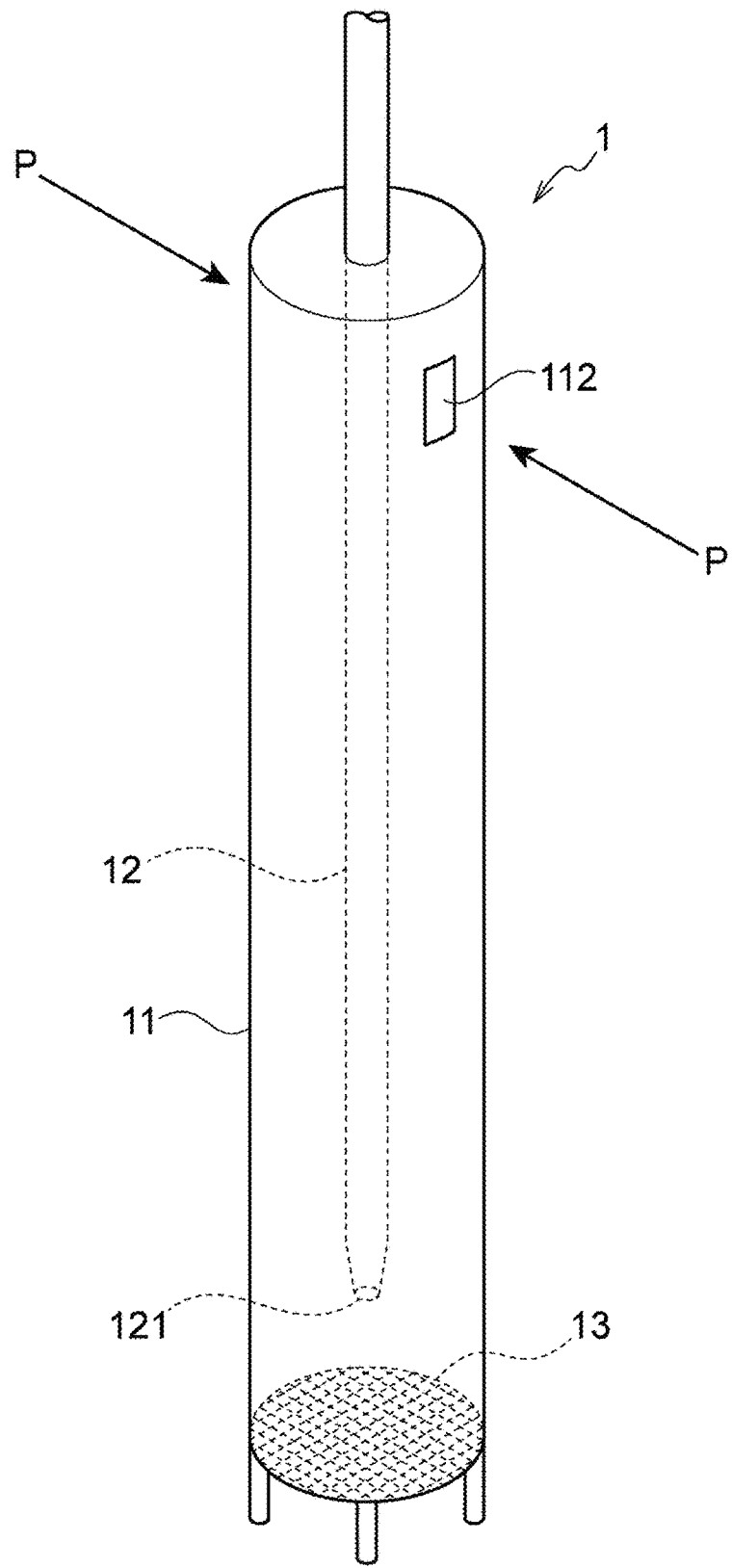
FIG. 2 is a perspective view illustrating the configuration of the culture solution aspirator according to the first embodiment of the present invention.
Figure 3:
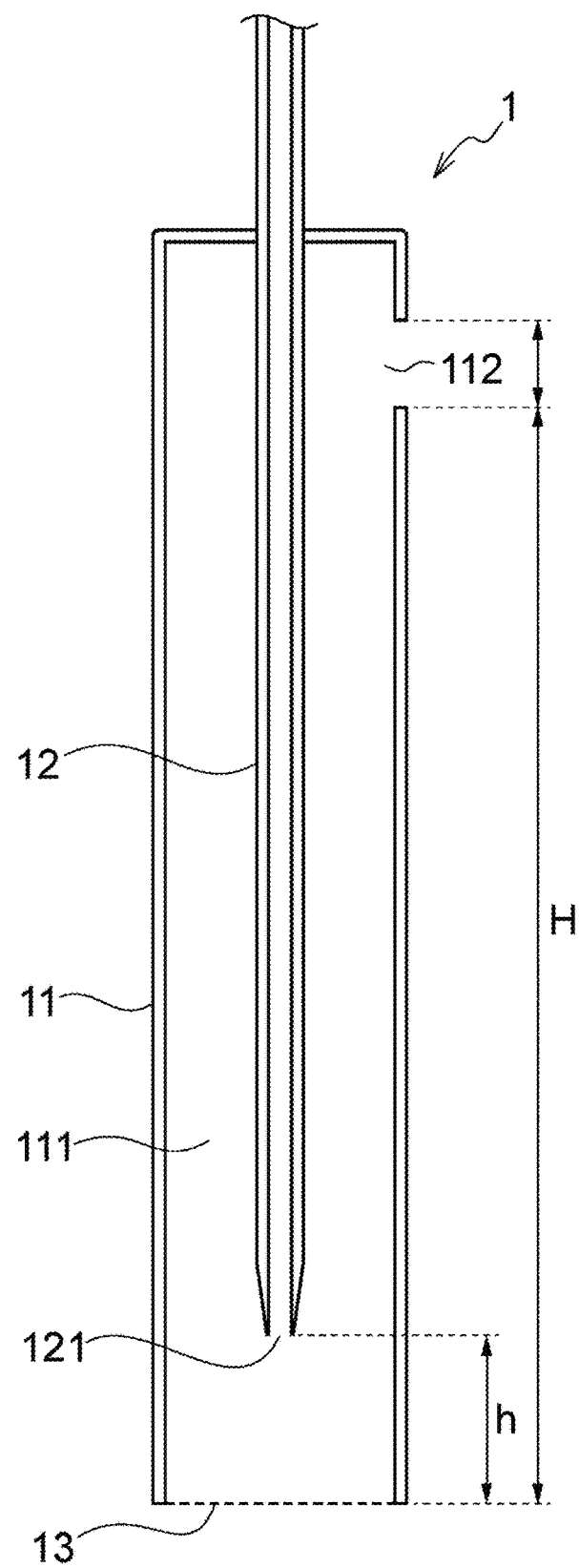
FIG. 3 is a cross-sectional view (cross section taken along the P-P line in FIG. 2) illustrating the configuration of the culture solution aspirator according to the first embodiment of the present invention.

Referring to FIGS. 1 to 3, the configuration of the culture solution aspirator 1 according to the first embodiment of the present invention will be described. The culture solution aspirator 1 has a double-tube structure comprising outer tube 11 and inner tube 12 inserted in lumen 111 of the outer tube 11. The outer tube 11 has a distal end and a proximal end and has the lumen 111 from the distal end to the proximal end. The proximal end is defined as a lower side in the direction of insertion of the culture solution aspirator 1 into the suspension culture vessel 2 (lower portion in the drawings), and the distal end is defined as an upper side in this direction (upper portion in the drawings). The inner tube 12 also has a distal end and a proximal end and has a lumen from the distal end to the proximal end.

The outer tube 11 comprises filter 13 through which a culture solution is passed, without being permeable to aggregates of cells. The position at which the filter 13 is provided in the outer tube 11 is not particularly limited as long as the site may be immersed in the culture solution when the culture solution aspirator is inserted in the suspension culture vessel 2. As shown in the drawings, for example, the filter can be disposed at a front end in the direction of insertion into the suspension culture vessel 2.

A metal, glass, or a resin material such as polystyrene or polypropylene conventionally used in the culture of cells can be suitably used as a material for the outer tube 11. These materials may be coated in order to prevent the adhesion of cells or proteins. Examples of the coating agent include 2-methacryloyloxyethyl phosphorylcholine (MPC) polymer, Pluronic F127, poly(2-methoxyethyl acrylate) (PMEA), poly(methacrylic acid 2-hydroxyethyl methacrylate) (pHEMA), polyethylene glycol (PEG), and polyvinyl alcohol (PVA). MPC polymer is preferred.

The shape, diameter, or length of the outer tube 11 is not particularly limited. The shape can be a cylinder or a polygonal prism, and the outer tube may be formed partially or wholly in a tapered form. The diameter (inside diameter)

and the length may be appropriately set according to the capacity (i.e., culture scale) of the suspension culture vessel 2.

For example, when the capacity of the suspension culture vessel 2 is 250 mL, the outer tube has a diameter on the order of 0.5 cm and a length on the order of 5 to 10 cm. When the capacity is 2000 L, the outer tube has a diameter on the order of 10 cm and a length on the order of 200 to 250 cm. Thus, the outer tube 11 has a diameter of, for example, 0.5 to 10 cm, and a length of 5 to 250 cm. The length of the outer tube 11 is larger by 5% or more, preferably 10% or more, more preferably 15% or more, further preferably 20% or more, particularly preferably 25% or more, than depth D (see FIG. 1) of the culture solution.

A resin mesh or membrane such as nylon or polyester conventionally used in the separation of cells can be suitably used for the filter 13. A material for the filter 13 may be a resin as well as a metal, glass, fiber, or the like. These materials may be coated in order to prevent the adhesion of cells or proteins. Examples of the coating agent include 2-methacryloyloxyethyl phosphorylcholine (MPC) polymer, Pluronic F127, poly(2-methoxyethyl acrylate) (PMEA), poly(methacrylic acid 2-hydroxyethyl methacrylate) (pHEMA), polyethylene glycol (PEG), and polyvinyl alcohol (PVA). MPC polymer is preferred. The mesh size or the pore size may be appropriately set according to the sizes of cells of interest to be cultured and aggregates to be formed by the cells. The shape, diameter, or thickness of the filter 13 is not particularly limited. The shape can be a circle or a polygon. The diameter can be, for example, 0.5 to 10 cm, in conformity to the diameter of the outer tube, and may be smaller than the diameter of the outer tube 11. In order to enhance the efficiency of culture solution replacement, the filter 13 may be provided at the outer periphery of the outer tube 11, as in the second embodiment mentioned later. The thickness is on the order of, for example, 0.05 to 2 mm. The filter 13 may be replaceably provided. The filter 13 may be configured to constitute a three-dimensional shape (e.g., a sphere, a deformed solid of a sphere, a circular cone, a circular truncated cone, and a polyhedron) integrally with a portion or the whole of the outer tube 11.

In the present invention, the cells of interest to be cultured may include a wide range of cells that may proliferate under suspension culture and form aggregates. In this context, the "aggregate" may comprise cells as well as a carrier to which the cells are attached. The carrier for suspension culture to which cells are capable of adhering is called microcarrier, and particles made of polystyrene, cellulose, dextran, or the like are commercially available. The cells of interest to be cultured according to the present invention may include a wide range of cells that have the ability to be attached to such a carrier and may be suspension-cultured in a state attached to the carrier.

One or two or more types of cells of interest to be cultured can be used.

Examples thereof include pluripotent stem cells, multipotent stem cells, pluripotent or multipotent stem cell-derived cells, cancer cells, and established cell lines.

The "pluripotent stem cells" refer to embryonic stem cells (ES cells) and cells potentially having pluripotent differentiation similar thereto, i.e., the ability to differentiate into various tissues (endoderm, mesoderm, and ectoderm) of the living body. Examples of the cells having pluripotent differentiation similar to that of the ES cells include "induced pluripotent stem cells" (also referred to as "iPS cells" herein).

Available "ES cells" include murine ES cells such as various murine ES cell lines established by inGenious Targeting Laboratory, Riken (Institute of Physical and Chemical Research), and the like, and human ES cells such as various human ES cell lines established by Thomson et al. from University of Wisconsin (USA), NIH (USA), Riken, Kyoto University, and Cellartis. For example, CHB-1 to CHB-12 lines, RUES1 line, RUES2 line, and HUES1 to HUES28 lines from NIH, H1 line and H9 line from WiCell Research, and KhES-1 line, KhES-2 line, KhES-3 line, KhES-4 line, KhES-5 line, SSES1 line, SSES2 line, and SSES3 line from Riken can be used as the human ES cell lines.

The "induced pluripotent stem cells" refer to cells that are obtained by reprograming mammalian somatic cells or undifferentiated stem cells by introducing particular factors (nuclear reprogramming factors). At present, there are various "induced pluripotent stem cells" and iPS cells established by Yamanaka, et al. by introducing the 4 factors Oct3/4, Sox2, Klf4, c-Myc into murine fibroblasts (Takahashi K, Yamanaka S., Cell, (2006) 126: 663-676); iPS cells derived from human cells, established by introducing similar 4 factors into human fibroblasts (Takahashi K, Yamanaka S., et al. Cell, (2007) 131: 861-872.); Nanog-iPS cells established by sorting cells using expression of Nanog as an indicator after introduction of the 4 factors (Okita, K., Ichisaka, T., and Yamanaka, S. (2007). Nature 448, 313-317.); iPS cells produced by a method not using c-Myc (Nakagawa M, Yamanaka S., et al. Nature Biotechnology, (2008) 26, 101-106); iPS cells established by introducing 6 factors by a virus-free method (Okita K et al. Nat. Methods 2011 May; 8(5): 409-12, Okita K et al. Stem Cells. 31 (3) 458-66); and the like may be also used. Also, induced pluripotent stem cells established by introducing the 4 factors OCT3/4, SOX2, NANOG, and LIN28 by Thomson et al. (Yu J., Thomson JA. et al., Science (2007) 318: 1917-1920.); induced pluripotent stem cells produced by Daley et al. (Park I H, Daley G Q. et al., Nature (2007) 451: 141-146); induced pluripotent stem cells produced by Sakurada et al. (Japanese Unexamined Patent Application Publication No. 2008-307007) and the like may be used.

In addition, any of known induced pluripotent stem cells known in the art described in all published articles (for example, Shi Y., Ding S., et al., Cell Stem Cell, (2008) Vol 3, Issue 5, 568-574; Kim J B., Scholer H R., et al., Nature, (2008) 454, 646-650; Huangfu D., Melton, D A., et al., Nature Biotechnology, (2008) 26, No. 7, 795-797) or patents (for example, Japanese Unexamined Patent Application Publication No. 2008-307007, Japanese Unexamined Patent Application Publication No. 2008-283972, US2008-2336610, US2009-047263, WO2007-069666, WO2008-118220, WO2008-124133, WO2008-151058, WO2009-006930, WO2009-006997, WO2009-007852).

Available induced pluripotent cell lines include various iPS cell lines established by NIH, Institute of Physical and Chemical Research (Riken), Kyoto University and the like. Examples of such human iPS cell lines include HiPS-RIKEN-1A line, HiPS-RIKEN-2A line, HiPS-RIKEN-12A line, and Nips-B2 line from Riken, Ff-WJ-18 line, Ff-I01s01 line, Ff-I01s02 line, Ff-I01s04 line, Ff-I01s06 line, Ff-I14s03 line, Ff-I14s04 line, QHJI01s01 line, QHJI01s04 line, QHJI14s03 line, QHJI14s04 line253G1 line, 201B7 line, 409B2 line, 454E2 line, 606A1 line, 610B1 line, and 648A1 line from Kyoto University, and MyCell iPS Cells (21525.102.10A) line and MyCell iPS Cells (21526.101.10A) from CDI.

Easily available induced pluripotent cell lines include various iPS cells lines established by NIH, Riken, Kyoto University and the like. Examples of such human iPS cells lines include HiPS-RIKEN-1A line, HiPS-RIKEN-2A line, HiPS-RIKEN-12A line, and Nips-B2 line from Riken, and 253G1 line, 201B7 line, 409B2 line, 454E2 line, 606A1 line, 610B1 line, and 648A1 line from Kyoto University.

The pluripotent or multipotent stem cell-derived cells refer to cells into which the differentiation of pluripotent or multipotent stem cells is induced. Examples thereof include, but are not particularly limited to, myocardial cells, definitive endoderm cells, primitive gut tube cells, posterior foregut cells, pancreatic progenitor cells, neural progenitor cells, liver cells and vascular endothelia cells.

Examples of the cancer cells include, but are not particularly limited to, cancer cells derived from lung cancer, kidney cancer, urothelial cancer, colorectal cancer, prostate cancer, glioblastoma multiforme, ovary cancer, pancreatic cancer, breast cancer, melanoma, liver cancer, urinary bladder cancer, stomach cancer and esophageal cancer.

Examples of the established cell lines include, but are not particularly limited to, MRC-5, GL37, Vero and CHO.

The size of these cells is usually on the order of 10 to 20 µm. The size of the cell aggregates is usually on the order of 20 to 1000 µm and is, particularly, on the order of 20 to 400 µm according to the purpose of culture.

Thus, provided that the mesh size or the pore size is set to be smaller than the size of cell aggregates of interest, cell aggregates having a size smaller than the size of interest, non-aggregated cells and the culture solution can be passed through the filter 13, without being permeable to cell aggregates having a size equal to or larger than the size of interest. The non-aggregated cells may include dead cells. In the case of using a membrane, its pore size is on the order of, for example, 15 to 995 µm, for example, 15, 50, 100, 150, 200, 250, 300, 350, 395, 450, 500, 550, 600, 650, 700, 750, 800, 850, or 995 µm, preferably on the order of 15 to 395 µm, particularly, on the order of 15 to 40 µm. Alternatively, the pore size is preferably smaller by approximately 5 µm than the size of cell aggregates of interest. The mesh size (opening size) may also be the same size as the pore size.

The inner tube 12 comprises suction port 121 which aspirates the culture solution passed through the filter 13. From the suction port 121, cell aggregates having a size smaller than the size of interest, non-aggregated cells, and cell debris are also aspirated together with the culture solution passed through the filter 13. The culture solution, the cell aggregates having a size smaller than the size of interest and the non-aggregated cells aspirated from the suction port 121 flow through the lumen of the inner tube 12 and are discharged to the outside of the suspension culture vessel 2. The position at which the suction port 121 is provided in the inner tube 12 is not particularly limited as long as the site may be immersed in the culture solution passed through the filter 13 when the culture solution aspirator is inserted in the suspension culture vessel 2. The suction port is preferably disposed at a front end (proximal end) in the direction of insertion into the suspension culture vessel 2.

The shape or diameter of the suction port 121 is not particularly limited. The shape can be a round hole or a polygonal hole. The diameter (inside diameter) is on the order of, for example, 0.01 to 3 cm.

A material for the inner tube 12 can be the same as that for the outer tube 11, and a metal, glass, or a resin material such as polystyrene or polypropylene is suitably used. These materials may be coated (e.g., coated with MPC) in order to prevent the adhesion of cells or proteins.

The shape, diameter, or length of the inner tube 12 is not particularly limited. The shape can be a cylinder or a polygonal prism, and the inner tube may be formed partially or wholly in a tapered form. The diameter (inside diameter) is on the order of, for example, 0.04 to 3 cm. Distance h (see FIG. 3) between the filter 13 provided at the proximal end of the outer tube 11 and the suction port 121 provided at the proximal end of the inner tube 12 is not particularly limited and is preferably on the order of $\frac{1}{10}$ to $\frac{1}{50}$ of the length of the outer tube.

The opposite end (distal end) of the inner tube 12 with respect to the suction port 121 is connected to a pump serving as a negative pressure source for aspirating the culture solution, etc. A pump conventionally used for sending a culture solution in a cell culturing apparatus can be adopted. The aspiration of the culture solution by the pump may be appropriately set according to the capacity (culture scale) of the suspension culture vessel 2. For example, when the capacity of the suspension culture vessel 2 is 250 mL, the aspiration is performed at a rate on the order of 0.1 to 10 ml/min. When the capacity is 2000 L, the aspiration is performed at a rate on the order of 0.8 to 80 L/min. The aspiration of the culture solution by the pump can be performed continuously or intermittently.

The outer tube 11 has air hole 112 which communicates the lumen 111 with the outside, distally in the direction of insertion into the suspension culture vessel 2. The air hole 112 functions to allow negative pressure in the lumen 111 of the outer tube 11 to escape to the outside (vapor phase in the suspension culture vessel 2).

The shape or size of the air hole 112 is not particularly limited. The shape can be a quadrangle, a polygon, a circle or an ellipse. The size can be a size sufficient for allowing negative pressure in the lumen 111 of the outer tube 11 to escape to the outside.

The outer tube 11 and the inner tube 12 are joined so as not to interfere with the flow of air in the lumen 111 of the outer tube 11. For example, as shown in FIG. 3, the outer tube 11 and the inner tube 12 can be joined at a site where the inner tube 12 penetrates the upper end face of the outer tube 11. Alternatively, a supporting member may be provided to protrude from the outer tube 11 to the lumen 111, and the inner tube 12 can be joined to the supporting member.

In another mode, the outer tube 11 and the inner tube 12 may not be joined. For example, as shown in FIG. 1, the outer tube 11 may be joined to the bottom of the suspension culture vessel 2, and the inner tube 12 can be joined to the upper surface of the suspension culture vessel 2 at a site where the inner tube 12 penetrates the upper surface of the suspension culture vessel 2.

If the aspiration of the culture solution, etc. from the suction port 121 of the inner tube 12 applies an excess of negative pressure to the lumen 111 of the outer tube 11, the filter 13 might be clogged with cell aggregates having a size equal to or larger than the mesh size or the pore size, due to too large suction pressure of the culture solution, etc. via the filter 13. The clogging of the filter 13 disables culture solution replacement, or disables uniform filtration throughout the filter surface and thereby delays culture solution replacement. The negative pressure in the lumen 111 can escape from the air hole 112 to the outside, thereby preventing the application of an excess of negative pressure to the lumen 111. This prevents the filter 13 from being clogged with cell aggregates having a size equal to or larger than the mesh size or the pore size, while only cell aggregates having the size of interest can remain in the suspension culture vessel 2 by passing cell aggregates having a size smaller than the size of interest and non-aggregated cells through the filter 13. Furthermore, if the filter 13 is clogged, the negative pressure in the lumen 111 is canceled owing to air coming into the lumen 111 from the air hole 112 by merely stopping aspiration through the inner tube 12. Therefore, the clogging can be resolved without back-flow work which is required for resolving clogging in culture solution replacement using a usual filter.

The position at which the air hole 112 is provided in the outer tube 11 is not particularly limited as long as the site may be positioned in a vapor phase in the suspension culture vessel 2 (the site is not immersed in the culture solution) when the outer tube 11 is inserted into the suspension culture vessel 2. When the culture solution aspirator 1 is placed such that the filter 13 is positioned in a lower portion thereof, the air hole 112 needs to be disposed above the suction port 121. When the filter 13 in the outer tube 11 is disposed at a front end (proximal end) in the direction of insertion into the suspension culture vessel 2, the distance (see reference symbol H in FIG. 3) between the filter 13 and the air hole 112 is preferably much larger than depth D (see FIG. 1) of the culture solution in the suspension culture vessel 2. The distance H is larger by 105% or more, preferably 110% or more, more preferably 115% or more, further preferably 120% or more, particularly preferably 125% or more, than the depth D of the culture solution.

Figure 4:
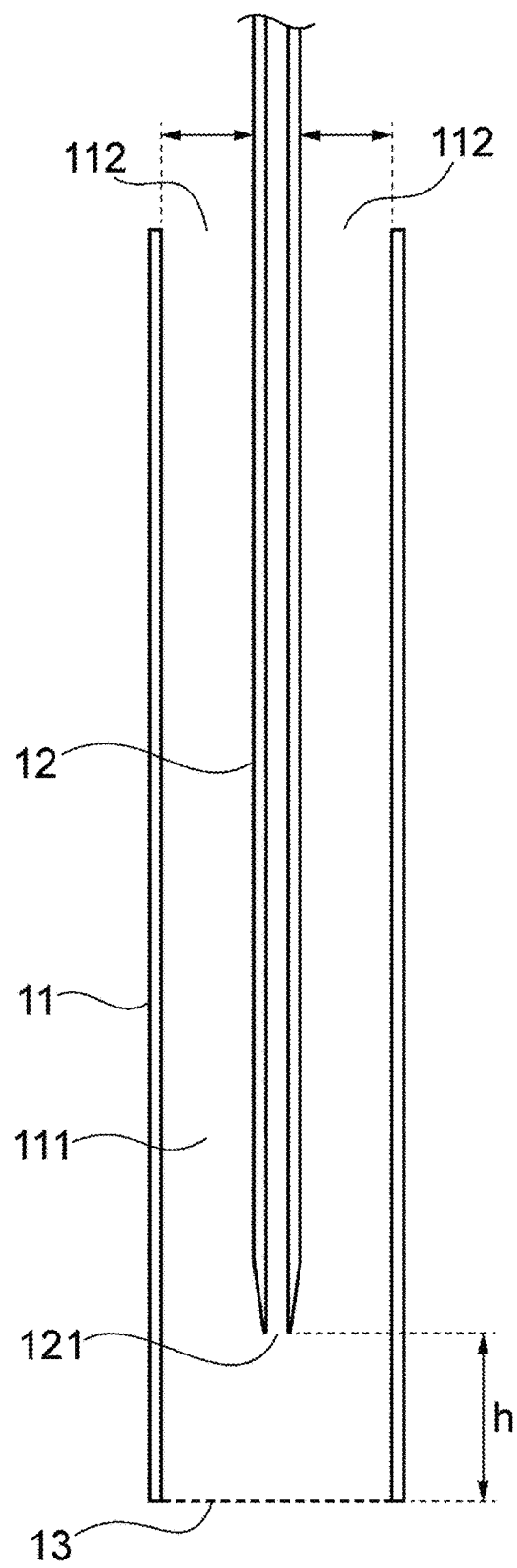
FIG. 4 is a cross-sectional view illustrating the configuration of a modification of the culture solution aspirator according to the first embodiment of the present invention.

As shown in FIG. 4, the air hole 112 may be configured to serve as an insertion port for the inner tube 12 in the outer tube 11. In this case, the gap between the lumen surface of the outer tube 11 and the outer surface of the inner tube 12 at the insertion port functions as the air hole 112.

Figure 5:
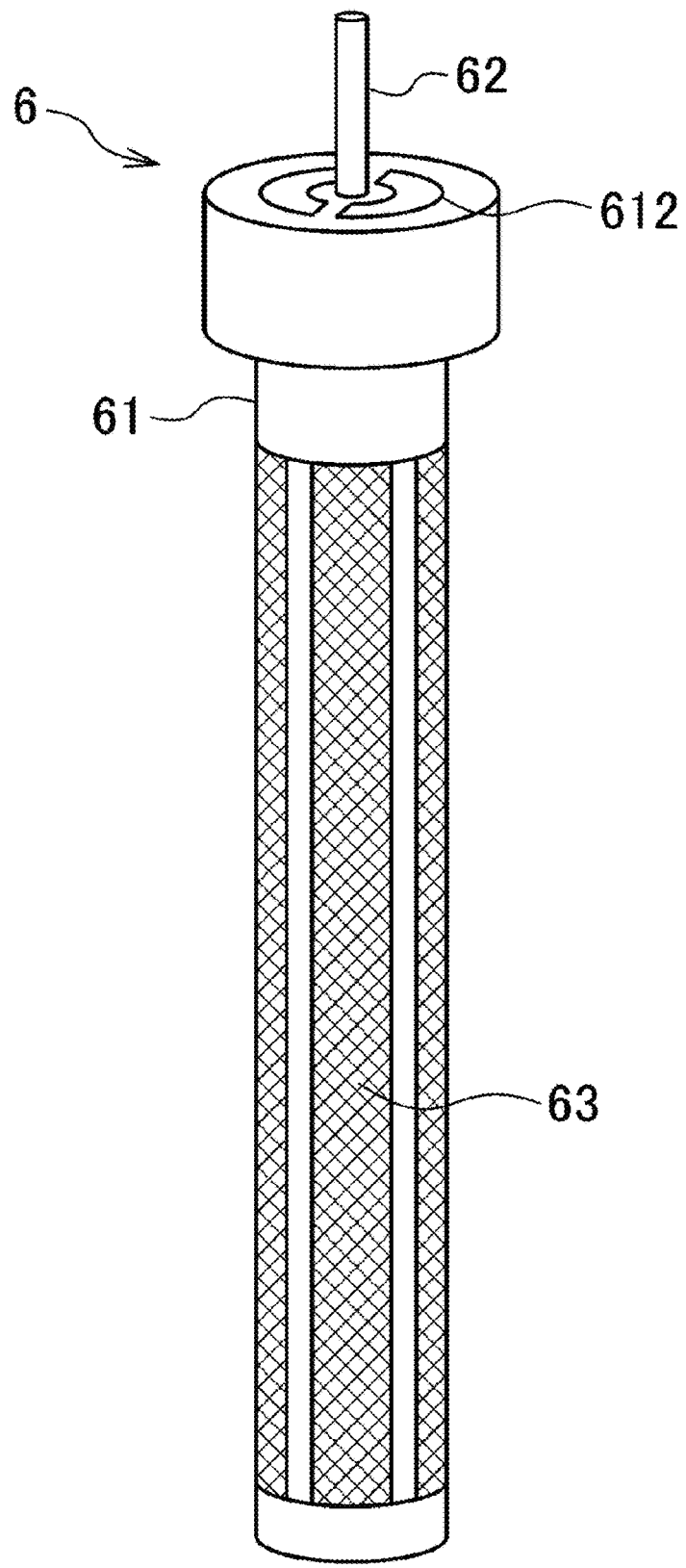
FIG. 5 is a diagram illustrating the configuration of the culture solution aspirator, particularly, an outer tube, according to the second embodiment of the present invention.
Figure 6:
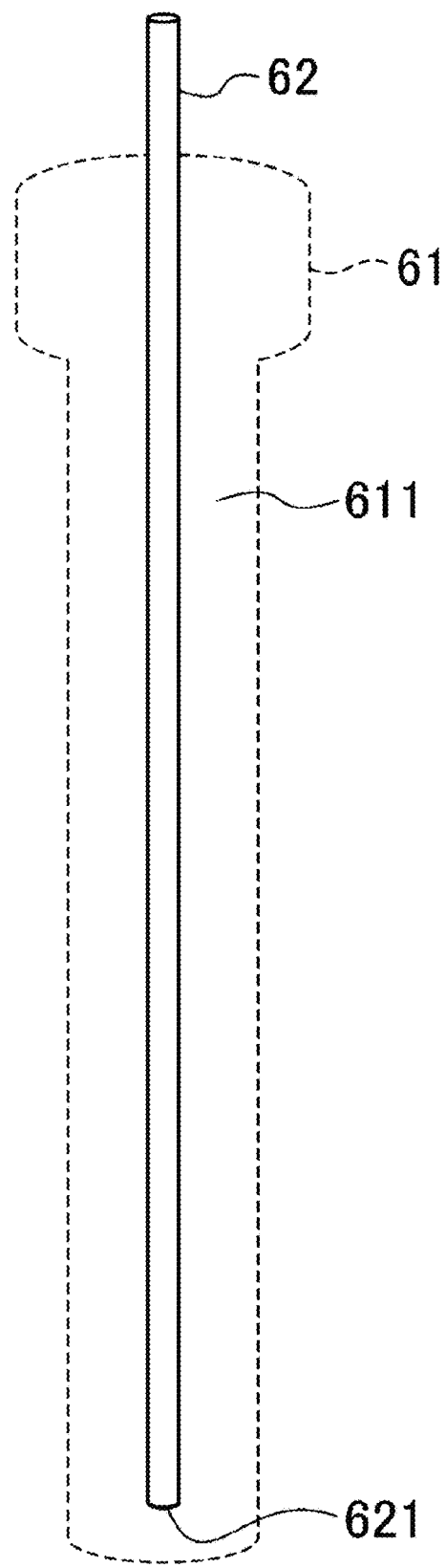
FIG. 6 is a diagram illustrating the configuration of the culture solution aspirator, particularly, an inner tube, according to the second embodiment of the present invention.

Referring to FIGS. 5 and 6, the configuration of culture solution aspirator 6 according to the second embodiment of the present invention will be described. The culture solution aspirator 6 differs from the culture solution aspirator 1 according to the first embodiment in that filter 63 is provided at the outer periphery of outer tube 61. Hereinafter, the configuration of the culture solution aspirator 6 may be the same as that of the culture solution aspirator 1 unless otherwise specified.

The filter 63 can be attached to an open window disposed in the outer tube 61. Cell aggregates having a size smaller than the size of interest, non-aggregated cells, and cell debris are passed through the filter 63, introduced to lumen 611, aspirated from suction port 621 of inner tube 62, and after flowing through the lumen of the inner tube 62, discharged to the outside.

The materials, shapes, diameters, and lengths of the outer tube 61 and the inner tube 62 are the same as those of the culture solution aspirator 1 according to the first embodiment.

The position at which the filter 63 is provided in the outer tube 61 is not particularly limited as long as the site may be immersed in the culture solution when the culture solution aspirator is inserted in the suspension culture vessel 2. The filter 63 can be disposed at the outer periphery of the outer tube 61 such that the filter is located with an arbitrary area in an arbitrary region between a front end (proximal end) in the direction of insertion into the suspension culture vessel 2 and the position at which the air hole 612 is provided. One or two or more filters 63 can be provided at the outer periphery of the outer tube 61. The ratio of the total area of the filter(s) 63 to the outer periphery of the outer tube 61 is, for example, 10%, 20%, or 30%, preferably 40%, 50%, or 60%, more preferably 70% or 80%, particularly preferably 90% or 95%. The shape or thickness of the filter 63 is not particularly limited. The shape can be a circle or a polygon. The thickness is on the order of, for example, 0.1 to 2 mm.

The position at which the suction port 621 is provided in the inner tube 62 is not particularly limited as long as the site may be immersed in the culture solution passed through the filter 63 when the culture solution aspirator is inserted in the suspension culture vessel 2. The suction port is preferably disposed at a front end (proximal end) in the direction of insertion into the suspension culture vessel 2. The shape and diameter of the suction port 621 are the same as those of the culture solution aspirator 1 according to the first embodiment.

The position at which the air hole 612 is provided in the outer tube 61 is not particularly limited as long as the site may be positioned in a vapor phase in the suspension culture vessel 2 (the site is not immersed in the culture solution) when the outer tube 61 is inserted into the suspension culture vessel 2. When the culture solution aspirator 6 is placed such that the filter 63 is positioned in a lower portion thereof, the air hole 612 needs to be disposed above the suction port 621 and the filter 63.

The filter 63 may be partially positioned in a vapor phase in the suspension culture vessel 2 without being immersed in the culture solution when the culture solution aspirator is inserted in the suspension culture vessel 2. For example, when the level of the culture solution gets lower in association with the discharge of the culture solution, the upper portion of the filter 63 is exposed to a vapor phase in the suspension culture vessel 2. Thus, when the filter 63 is partially exposed to the vapor phase in the suspension culture vessel 2 without being immersed in the culture solution, this portion of the filter 63 may function, as in the air hole 612, to allow the negative pressure in the lumen 611 of the outer tube 61 to escape to the outside (vapor phase in the suspension culture vessel 2).

The suspension culture vessel 2 is an airtight tank having the function of retaining cells and a culture solution (see FIG. 1 again).

The culture solution supply channel 3 functions to supply a fresh culture solution continuously or intermittently into the suspension culture vessel 2. Preferably, the culture solution supply channel 3 continuously supplies a culture solution. In this case, the cell culturing apparatus A may be configured as a perfusion culturing apparatus which discharges the culture solution from the suspension culture vessel 2 by the culture solution aspirator 1 while supplying a fresh culture solution in the same amount as the amount of discharged culture solution into the suspension culture vessel 2 by the culture solution supply channel 3.

The air supply channel 4 functions to supply air into the suspension culture vessel 2. The air supply channel 4 is preferably configured to extent along the bottom of the suspension culture vessel 2 and to eject air bubbles upward from near the bottom.

The stirrer 5 that can be adopted is configured to stir the culture solution in the suspension culture vessel 2, for example, by rotating or moving up and down the stirring bar 51.

A tank, a tube, or an instrument conventionally used in cell culture can be appropriately adopted for the suspension culture vessel 2, the culture solution supply channel 3, the air supply channel 4 and the stirrer 5. A wide range of instruments, etc. may be adopted as long as these instruments, etc. may exert the functions mentioned above.

In addition to these members, the cell culturing apparatus A may have a supercooling unit (thermal jet) for controlling the temperature of the culture solution in the suspension culture vessel 2, or a probe for detecting, for example, the temperature of the culture solution, the concentration of oxygen, or the concentration of a nutritional factor or the like. The cell culturing apparatus may have a system unit which controls the supercooling unit on the basis of the detected value of the temperature by the probe in response to output from the probe. The system unit may control the amount of air supplied by the air supply channel 4 or the amounts of the culture solution supplied and discharged by the culture solution supply channel 3 and the culture solution aspirator 1, on the basis of the detected value of the concentration of oxygen or the concentration of a nutritional factor or the like by the probe in response to output from the probe.

The cell culturing apparatus A according to the present invention can replace the culture solution with the fresh one by preventing the filter 13 from being clogged with cell aggregates having a size equal to or larger than the mesh size or the pore size, while only cell aggregates having the size of interest remain in the suspension culture vessel 2 by passing cell aggregates having a size smaller than the size of interest, non-aggregated cells, and cell debris through the filter 13 for removal from the suspension culture vessel 2. Thus, the cell culturing apparatus A according to the present invention eliminates the need of time to temporarily stop the stirrer 5 and wait for the spontaneous precipitation of cells, for culture solution replacement even at the time of large-scale culture. Thus, the cell culturing apparatus can shorten the time required for culture solution replacement and can also prevent unstable and inhomogeneous proliferation or properties of cells. Particularly, the cell culturing apparatus A according to the present invention can suppress an excess of aggregation (formation of aggregates having a much larger size than the size of interest) of cells conventionally formed by temporarily stopping the stirring of a culture solution.

[Cell culturing apparatus (second aspect)]

The cell culturing apparatus according to the present invention (second aspect) comprises a suspension culture vessel and a culture solution aspirator. The culture solution aspirator has a proximal end and a distal end, and is configured such that a tube port at the proximal end serves as a suction port for a culture solution. A tube port at the distal end is connected to a pump. The suspension culture vessel comprises a stirrer for stirring a culture solution, and a filter through which a culture solution is passed. The filter divides the inside of the suspension culture vessel into a first region provided with the stirrer and a second region in which the culture solution aspirator is inserted.

Figure 7:
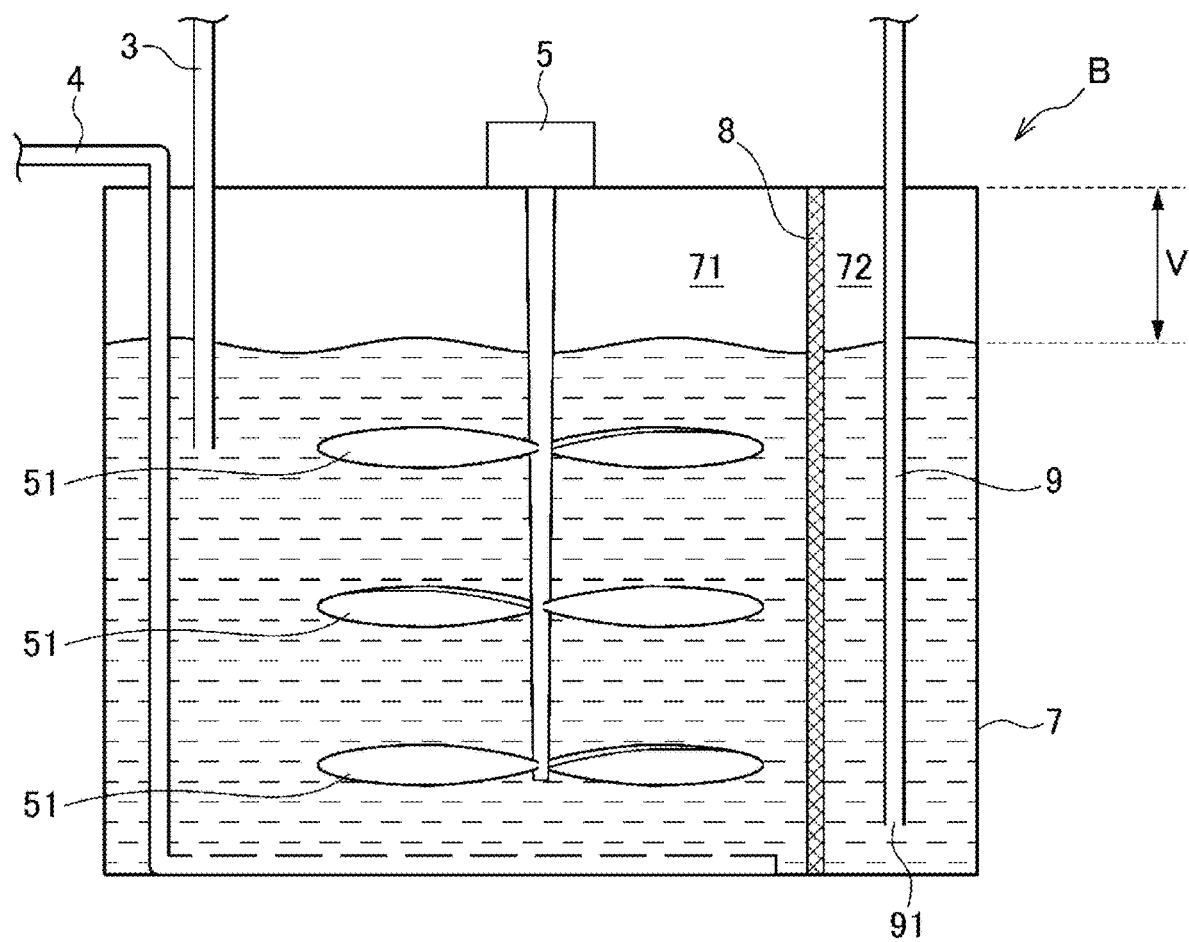
FIG. 7 is a diagram illustrating the configuration of the cell culturing apparatus according to the present invention (second aspect).

Referring to FIG. 7, the configuration of cell culturing apparatus B according to the present invention (second aspect) will be described. The cell culturing apparatus B comprises suspension culture vessel 7 which retains cells and a culture solution, and culture solution aspirator 9 which discharges the culture solution in the suspension culture vessel 7 to the outside.

In the drawing, reference numeral 3 denotes a culture solution supply channel, and reference numeral 4 denotes an air supply channel. The culture solution supply channel 3 functions to supply a fresh culture solution continuously or intermittently into the suspension culture vessel 7. Preferably, the culture solution supply channel 3 continuously supplies a culture solution. In this case, the cell culture vessel B may be configured as a perfusion culturing apparatus which discharges the culture solution from the suspension culture vessel 7 by the culture solution aspirator 9 while supplying a fresh culture solution in the same amount as the amount of discharged culture solution into the suspension culture vessel 7 by the culture solution supply channel 3. The air supply channel 4 functions to supply air into the suspension culture vessel 7. The air supply channel 4 is preferably configured to extent along the bottom of the suspension culture vessel 7 and to eject air bubbles upward from near the bottom.

Reference numeral 5 denotes a stirrer comprising stirring bar 51. The stirrer 5 stirs the culture solution in the suspension culture vessel 7 by rotating or moving up and down the stirring bar 51.

A tube or an instrument conventionally used in cell culture can be appropriately adopted for the culture solution supply channel 3, the air supply channel 4, the stirrer 5 and the culture solution aspirator 9. A wide range of instruments, etc. may be adopted as long as these instruments, etc. may exert the functions mentioned above.

The culture solution aspirator 9 can have a single tubular structure. The culture solution aspirator 9 has a distal end and a proximal end and has a lumen from the distal end to the proximal end. The proximal end is defined as a lower side in the direction of insertion of the culture solution aspirator 9 into the suspension culture vessel 7 (lower portion in the drawings), and the distal end is defined as an upper side in this direction (upper portion in the drawings).

The culture solution aspirator 9 comprises suction port 91 which aspirates a culture solution. From the suction port 91, cell aggregates having a size smaller than the size of interest, non-aggregated cells, and cell debris are also aspirated together with the culture solution. The culture solution, the cell aggregates having a size smaller than the size of interest, the non-aggregated cells, and the cell debris aspirated from the suction port 91 flow through the lumen of the culture solution aspirator 9 and are discharged to the outside of the suspension culture vessel 7. The position at which the suction port 91 is provided in the culture solution aspirator 9 is not particularly limited as long as the site may be immersed in the culture solution when the culture solution aspirator is inserted in the suspension culture vessel 7. The suction port is preferably disposed at a front end (proximal end) in the direction of insertion into the suspension culture vessel 7.

The shape or diameter of the suction port 91 is not particularly limited. The shape can be a round hole or a polygonal hole. The diameter (inside diameter) is on the order of, for example, 0.01 to 3 cm.

The opposite end (distal end) of the culture solution aspirator 9 with respect to the suction port 91 is connected to a pump serving as a negative pressure source for aspirating the culture solution, etc. A pump conventionally used for sending a culture solution in a cell culturing apparatus can be adopted. The aspiration of the culture solution by the pump may be appropriately set according to the capacity (culture scale) of the suspension culture vessel 7. For example, when the capacity of the suspension culture vessel 7 is 250 mL, the aspiration is performed at a rate on the order of 0.1 to 10 ml/min. When the capacity is 2000 L, the aspiration is performed at a rate on the order of 0.8 to 80 L/min. The aspiration of the culture solution by the pump can be performed continuously or intermittently.

A metal, glass, or a resin material such as polystyrene or polypropylene conventionally used in the culture of cells can be suitably used as a material for the culture solution aspirator 9. These materials may be coated in order to prevent the adhesion of cells or proteins. Examples of the coating agent include 2-methacryloyloxyethyl phosphorylcholine (MPC) polymer, Pluronic F127, poly(2-methoxyethyl acrylate) (PMEA), poly(methacrylic acid 2-hydroxyethyl methacrylate) (pHEMA), polyethylene glycol (PEG), and polyvinyl alcohol (PVA). MPC polymer is preferred.

The shape, diameter, or length of the culture solution aspirator 9 is not particularly limited. The shape can be a cylinder or a polygonal prism, and the culture solution aspirator may be formed partially or wholly in a tapered form. The diameter (inside diameter) and the length may be appropriately set according to the capacity (i.e., culture scale) of the suspension culture vessel 7. The diameter (inside diameter) is on the order of, for example, 0.04 to 3 cm.

The suspension culture vessel 7 is a tank having the function of retaining cells and a culture solution. The suspension culture vessel 7 comprises filter 8 through which a culture solution is passed, without being permeable to aggregates of cells. The filter 8 divides the inside of the suspension culture vessel 7 into first region 71 provided with the stirrer 5 and second region 72 in which the culture solution aspirator 9 is inserted. The culture solution supply channel 3 and the air supply channel 4 may be configured to supply a culture solution and air, respectively, to the first region 71 or the second region 72, and are preferably configured to supply a culture solution and air, respectively, to the first region 71. The filter 8 is provided to stretch in the vertically direction so as to form a portion that is immersed in the culture solution and a portion that is not immersed in the culture solution when the culture solution is charged into the suspension culture vessel 7. Preferably, the filter is provided vertically or substantially vertically, as shown in the drawing.

A resin mesh or membrane such as nylon or polyester conventionally used in the separation of cells can be suitably used for the filter 8. A material for the filter 8 may be a resin as well as a metal, glass, fiber, or the like. These materials may be coated in order to prevent the adhesion of cells or proteins. Examples of the coating agent include 2-methacryloyloxyethyl phosphorylcholine (MPC) polymer, Pluronic F127, poly(2-methoxyethyl acrylate) (PMEA), poly(methacrylic acid 2-hydroxyethyl methacrylate) (pHEMA), polyethylene glycol (PEG), and polyvinyl alcohol (PVA). MPC polymer is preferred. The mesh size or the pore size may be appropriately set according to the sizes of cells of interest to be cultured and aggregates to be formed by the cells. The shape of the filter 8 is appropriately designed according to the shape of the suspension culture vessel 7. The thickness of the filter 8 is not particularly limited and is on the order of, for example, 0.05 to 2 mm. The filter 8 may be replaceably provided.

As mentioned above, the size of the cells is usually on the order of 10 to 20 The size of the cell aggregates is usually on the order of 20 to 1000 μm and is, particularly, on the order of 20 to 400 μm according to the purpose of culture.

Thus, provided that the mesh size or the pore size is set to be smaller than the size of cell aggregates of interest, cell aggregates having a size smaller than the size of interest, non-aggregated cells and the culture solution can be passed through the filter 8, without being permeable to cell aggregates having a size equal to or larger than the size of interest. The non-aggregated cells may include dead cells. In the case of using a membrane, its pore size is on the order of, for example, 15 to 995 μm, for example, 15, 50, 100, 150, 200, 250, 300, 350, 395, 450, 500, 550, 600, 650, 700, 750, 800, 850, or 995 μm, preferably on the order of 15 to 395 μm, particularly, on the order of 15 to 40 μm. Alternatively, the pore size is preferably smaller by approximately 5 μm than the size of cell aggregates of interest. The mesh size (opening size) may also be the same size as the pore size.

In the filter 8, the portion that is not immersed in the culture solution (portion corresponding to reference numeral V in FIG. 7) functions to allow negative pressure in the second region 72 to escape to the first region 71 so that the pressure in the second region 72 and the pressure in the first region 71 are equilibrated.

In order to promote the flow of air, a through-hole may be disposed in the filter 8. The through-hole is disposed at a position that is not immersed in the culture solution, and is preferably disposed near the upper surface of the suspension culture vessel 7. In this case, the shape or size of the through-hole is not particularly limited. The shape can be a quadrangle, a polygon, a circle or an ellipse. The size can be a size sufficient for allowing negative pressure in the second region 72 to escape to the first region 71.

If the aspiration of the culture solution, etc. from the suction port 91 of the culture solution aspirator 9 applies an excess of negative pressure to the second region 72, the filter 8 might be clogged with cell aggregates having a size equal to or larger than the mesh size or the pore size, due to too large suction pressure of the culture solution, etc. via the filter 8. The clogging of the filter 8 disables culture solution replacement, or disables uniform filtration throughout the filter surface and thereby delays culture solution replacement. The negative pressure in the second region 72 can escape to the first region 71 via the portion that is not immersed in the culture solution in the filter 8, thereby preventing the application of an excess of negative pressure to the second region 72. This prevents the filter 8 from being clogged with cell aggregates having a size equal to or larger than the mesh size or the pore size, while only cell aggregates having the size of interest can remain in the first region 71 by passing cell aggregates having a size smaller than the size of interest and non-aggregated cells through the filter 8.

The cell culturing apparatus B may have a supercooling unit (thermal jet) for controlling the temperature of the culture solution in the suspension culture vessel 7, or a probe for detecting, for example, the temperature of the culture solution, the concentration of oxygen, or the concentration of a nutritional factor or the like. The cell culturing apparatus may have a system unit which controls the supercooling unit on the basis of the detected value of the temperature by the probe in response to output from the probe. The system unit may control the amount of air supplied by the air supply channel 4 or the amounts of the culture solution supplied and discharged by the culture solution supply channel 3 and the culture solution aspirator 9, on the basis of the detected value of the concentration of oxygen or the concentration of a nutritional factor or the like by the probe in response to output from the probe.

The cell culturing apparatus B according to the present invention can replace the culture solution with the fresh one by preventing the filter 8 from being clogged with cell aggregates having a size equal to or larger than the mesh size or the pore size, while only cell aggregates having the size of interest remain in the first region 71 by passing cell aggregates having a size smaller than the size of interest and non-aggregated cells through the second region 72. Thus, the cell culturing apparatus B according to the present invention eliminates the need of time to temporarily stop the stirrer 5 and wait for the spontaneous precipitation of cells, for culture solution replacement even at the time of large-scale culture. Thus, the cell culturing apparatus can shorten the time required for culture solution replacement and can also prevent unstable and inhomogeneous proliferation or properties of cells. Particularly, the cell culturing apparatus B according to the present invention can suppress an excess of aggregation (formation of aggregates having a much larger size than the size of interest) of cells conventionally formed by temporarily stopping the stirring of a culture solution.

[Cell Culturing Method]

The present invention also provides a cell culturing method using the cell culturing apparatus or the culture solution aspirator mentioned above. A feature of the cell culturing method according to the present invention is the discharge of a culture solution from a suspension culture vessel using the culture solution aspirator mentioned above. For the details thereof, see the description about the cell culturing apparatus or the culture solution aspirator mentioned above.

In the cell culturing method according to the present invention, the culture solution can be replaced with the fresh one with a stirrer actuated without temporarily stopping the stirring of the culture solution and waiting for the spontaneous precipitation of cells, even at the time of large-scale culture. Thus, the cell culturing method can shorten the time required for culture solution replacement and can efficiently produce a large amount of cells. Particularly, the cell culturing method according to the present invention can suppress an excess of aggregation (formation of aggregates having a much larger size than the size of interest) of cells conventionally formed by temporarily stopping the stirring of a culture solution. Thus, the cell culturing method can produce high-quality cells by preventing the inhibition of cell proliferation through an excess of cell aggregation or unstable and inhomogeneous properties of cells. In the case of performing large-scale medium replacement (e.g., 50 to 95% medium replacement) without stirring, the cell culturing method according to the present invention is also capable of shortening the required time because the method can be performed by precipitating cell aggregates to some extent.

This cell culturing method may be perfusion culture which involves discharging the culture solution from the suspension culture vessel by the culture solution aspirator while supplying a fresh culture solution into the suspension culture vessel. In the perfusion culture, the culture solution is replaced with the fresh one by discharging the culture solution concurrently with the supply thereof. In the perfusion culture, the amount of the culture solution supplied is preferably equal to the amount of the culture solution discharged.

When the cell culturing method is not based on perfusion culture, a given amount of the culture solution is discharged from the suspension culture vessel by the culture solution aspirator, and then, a fresh culture solution is supplied into the suspension culture vessel. The amount of the culture solution discharged is, for example, 10%, 20%, 30%, 40%, 50%, 60%, 70%, 80%, or 90%, preferably 60%, more preferably 70%, particularly preferably 80%, of the amount of the culture solution in the suspension culture vessel. Too large an amount of the culture solution discharged at one time might cause unexpected aggregation of cells. The amount of the culture solution supplied is preferably equal to the amount of the culture solution discharged.

The cell culturing method according to the present invention can be suitably applied to the maintenance or differentiation of pluripotent or multipotent stem cells or pluripotent or multipotent stem cell-derived cells in a suspension culture vessel. The cell culturing method according to the present invention is capable of culturing aggregates of pluripotent or multipotent stem cells having the size of interest efficiently, stably, and homogeneously even at the time of large-scale culture, and is therefore capable of producing a large amount of undifferentiated cells or differentiated cells efficiently, stably, and homogeneously. For the production of differentiated cells, a conventionally known differentiation induction approach can be applied thereto. For example, in Example mentioned later, DE (definitive endoderm) cells were induced from pluripotent stem cells. Pancreatic progenitor cells may be further induced from the DE cells. The induction of pancreatic progenitor cells from pluripotent stem cells can be performed by the following four steps (Nature Biotechnology, 2014, Vol. 32, No. 11, p. 1121-1133).

Step 1: Human pluripotent stem cells are induced to differentiate into definitive endoderm cells.

Step 2: The definitive endoderm cells are induced to differentiate into primitive gut tube cells.

Step 3: The primitive gut tube cells are induced to differentiate into posterior foregut cells.

Step 4: The posterior foregut cells are induced to differentiate into pancreatic progenitor cells.

Examples of the culture solution generally used in the present invention include BME medium, BGJb medium, CMRL 1066 medium, Glasgow MEM medium, improved MEM (IMEM) medium, improved MDM (IMDM) medium, Medium 199 medium, Eagle MEM medium, αMEM medium, DMEM medium (high glucose or low glucose), DMEM/F12 medium, Ham's medium, RPMI 1640 medium, Fischer's medium, and mixed media thereof.

Examples of the culture solution for ES cells or iPS cells include DMEM, DMEM/F12 and DME culture solutions containing 10 to 15% FBS (these culture solutions can further appropriately contain LIF, penicillin/streptomycin, puromycin, L-glutamine, non-essential amino acids, β-mercaptoethanol, etc.), and commercially available culture solutions for iPS cells, for example, a culture solution for murine ES cell culture (TX-WES culture solution, Thromb-X N.V.), a culture solution for primate ES cell culture (culture solution for primate ES/iPS cells, ReproCELL Inc.), a serum-free medium (mTESR, STEMCELL Technologies Inc.), and a medium for iPS/ES cell proliferation and a medium for regenerative medicine (StemFit(R), Ajinomoto Healthy Supply Co., Inc.). In addition, a culturing method using a medium containing no serum—is also exemplified (Sun N, et al., (2009), Proc Natl Acad Sci USA. 106: 15720-15725).

The culture solution for use in the present invention may be supplemented, if necessary, an amino acid, L-glutamine, GlutaMAX (product name), a non-essential amino acid, vitamin, an antibiotic (e.g., antibiotic-antimycotic (also referred to as AA herein), penicillin, streptomycin, or a mixture thereof), an antimicrobial agent (e.g., amphotericin B), an antioxidant, pyruvic acid, a buffer, inorganic salts, etc., in addition to the components described above.

The culture solution of the present invention may also contain a differentiation inducing agent.

In the suspension culture, cells proliferate via aggregate formation by uniformizing culture solution components and the internal oxygen concentration of the culture solution by stirring or shaking. The suitable stirring rate is appropriately set according to a cell density and the size of a culture container. Excessive stirring or shaking places physical stress on the cells and inhibits cell aggregate formation. Thus, the stirring or shaking rate is controlled so as to be able to uniformize culture solution components and the internal oxygen concentration of the culture solution and so as not to inhibit aggregate formation.

The culture temperature is not particularly limited and is 30 to 40° C. (e.g., 37° C.). A carbon dioxide concentration in the culture container is on the order of, for example, 5%.

EXAMPLE

Example 1

The culture of human iPS cells and the induction of differentiation into DE (definitive endoderm) cells were performed under conditions given below using the cell culturing apparatus according to the present invention. In the present Example, the cell culturing apparatus and the culture solution aspirator shown in FIGS. 5 and 6 were used.

Cell: human iPS cell Ff-I14s04 line Culture solution volume in suspension culture vessel: 250 ml Stirrer: HiD 4×4 (Satake Chemical Equipment Mfg., Ltd.), amplitude of up-and-down motion of stirring blade: 20 mm, rate: 100 mm/s Aspirator Outer tube: metal, length: 8.5 cm, diameter: 1 cm Filter: MPC-coated polyester membrane (pore size: 27 μm, thickness: 0.05 mm), area occupying outside surface of outer tube: 2880 $cm^2$ Air hole: the air hole was disposed with an area of 50 $cm^2$ at the upper end (distal end) of the outer tube.

Inner tube: metal, length: 146 mm, diameter: 6.35

Suction port: the suction port was disposed with a diameter of 6.35 mm at a position 0.4 cm from the lower end (proximal end) of the outer tube.

iPS cells were inoculated ($2\times10^3$ cells/ml) to 250 ml of a culture solution of StemFit(R) (Ajinomoto Healthy Supply Co., Inc.) supplemented with Y-27632 (CAS RN: 129830-38-2) charged in the suspension culture vessel, and cultured for 1 day (culture day 1). Then, an amount of 40% of the culture solution in the suspension culture vessel was aspirated by the aspirator and discharged to the outside of the suspension culture vessel. The same amount of a culture solution for differentiation induction as the amount of discharged culture solution was added into the suspension culture vessel. Then, an amount of 40% of the culture solution in the suspension culture vessel was aspirated by the aspirator again and discharged to the outside of the suspension culture vessel. The same amount of a culture solution for differentiation induction as the amount of discharged culture solution was added into the suspension culture vessel, followed by the restart of culture. The culture solution for differentiation induction used was a medium containing the differentiation inducing factors described in the literature (Nature Biotechnology, 2014, Vol. 32, No. 11, p. 1121-1133), etc.

On culture day 2 and subsequent days, differentiation into DE (definitive endoderm) cells was continued. On culture days 2 and 3, the same culture solution replacement operation as described above was performed, and culture was performed for a total of 4 days. On culture day 4, successful differentiation into DE cells was confirmed. On culture day 4 and subsequent days, the DE cells are further induced to differentiate into insulin producing cells.

Figure 8:
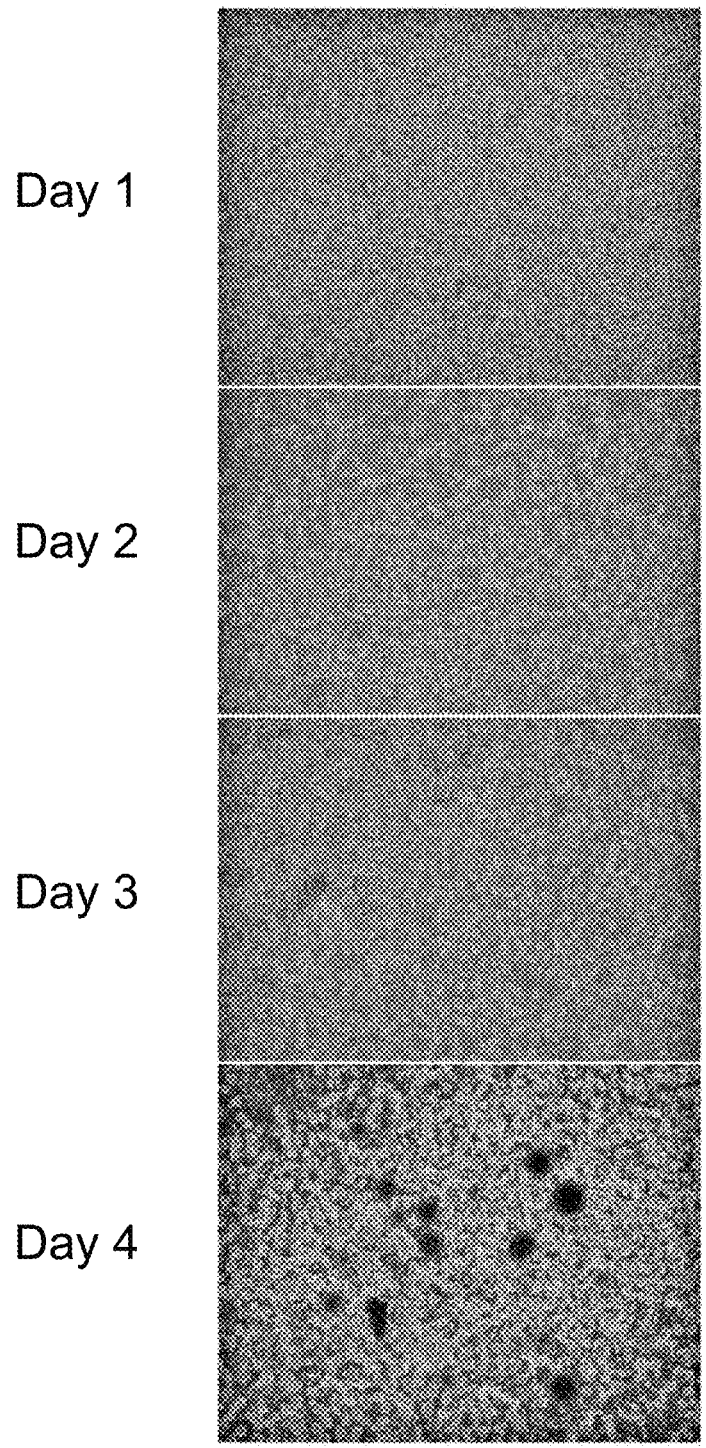
FIG. 8 shows phase-contrast micrographs of cells on culture day 4 in Example 1.

Cells immediately before culture solution replacement on culture days 1, 2 and 3 and cells on culture day 4 were collected and observed under a phase-contrast microscope. The phase-contrast micrographs of the cells are shown in FIG. 8. In order to confirm clogging, the filter was also observed after culture solution replacement on culture days 1, 2 and 3.

Figure 10:
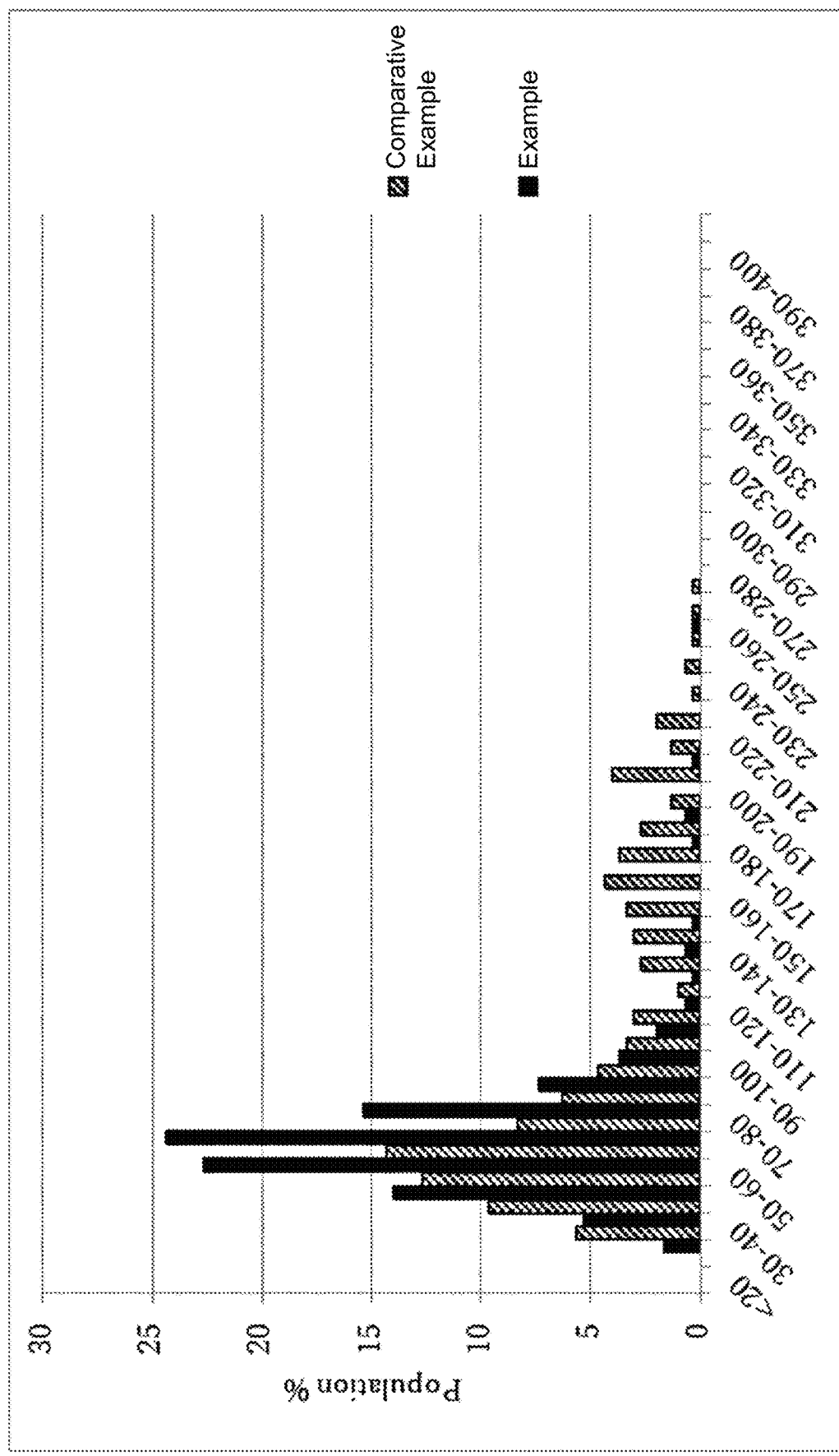
FIG. 10 shows size distributions of cell aggregates on culture day 4 in Example 1 and Comparative Example 1.

From the micrograph of the cells on culture day 4, the size distribution (diameter) of cell aggregates was measured using image analysis software. The results are shown in FIG. 10.

An excess of cell aggregation was not confirmed in the maintenance culture of iPS cells on culture day 1.

Culture days 2 to 4 are stages at which differentiation induction was carried out. On culture day 4, the cell aggregates were distributed mainly in the range of 30 to 90 μm. Most of aggregate populations had a size distribution centered at 60 μm, whereas the proportion of excessively large aggregates larger than 150 μm was small. The sizes of the cell aggregates had a mean of 65 μm and a standard deviation of 25 μm. At any point in time on culture days 1 to 4, it was confirmed that the cells were cultured as aggregates having a proper size.

The clogging of the filter with cell aggregates was not seen. It was able to be confirmed that the cell culturing apparatus according to the present invention can stably and homogeneously culture cell aggregates having the size of interest without temporarily stopping the stirring of the culture solution for culture solution replacement.

Comparative Example 1

Cells were suspension-cultured under the same conditions as in Example 1 except that: an electric pipette equipped with a disposable 50 ml pipette was used as a culture solution aspirator; and stirring was temporarily stopped during culture replacement.

Cells were inoculated ($2\times10^3$ cells/ml) to 250 ml of a culture solution charged in the suspension culture vessel, and cultured for 1 day (culture day 1). Then, the stirring of the culture solution was stopped so that the cells were spontaneously precipitated. An amount of 80% of the culture solution in the suspension culture vessel was aspirated by the aspirator and discharged to the outside of the suspension culture vessel. The same amount of a culture solution as the amount of discharged culture solution was added into the suspension culture vessel, followed by the restart of culture. On culture days 2 and 3, the same culture solution replacement operation as described above was performed, and culture was performed for a total of 4 days. On culture day 4, successful differentiation into DE cells was confirmed. On culture day 4 and subsequent days, the DE cells are further induced to differentiate into insulin producing cells.

Figure 9:
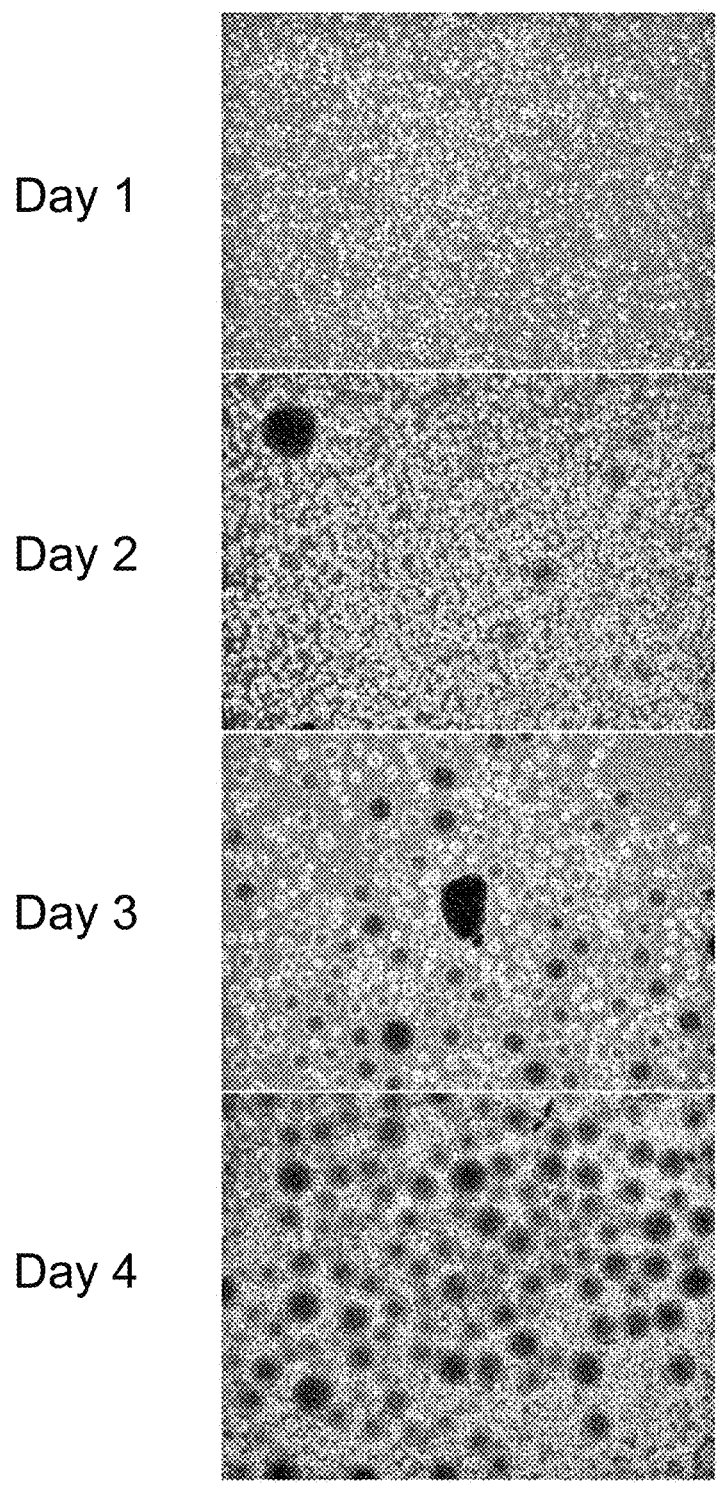
FIG. 9 shows phase-contrast micrographs of cells on culture day 4 in Comparative Example 1.

Cells immediately before culture solution replacement on culture days 1, 2 and 3 and cells on culture day 4 were collected and observed under a phase-contrast microscope. The phase-contrast micrographs of the cells are shown in FIG. 9.

From the micrograph of the cells on culture day 4, the size distribution of cell aggregates was measured using image analysis software. The results are shown in FIG. 10.

On culture day 1, an excess of cell aggregation started to occur. With increase in the number of culture days, the cell aggregates got excessively larger. On culture day 4, populations of cell aggregates having a size equal to or larger than 170 μm were seen. The sizes of the cell aggregates had a mean of 109 μm and a standard deviation of 60 Thus, the size distribution varied largely. This was probably because an excess of cell aggregation occurred while the stirring of the culture solution was temporarily stopped.

According to the present invention, the maintenance culture and differentiation induction of cells were able to be carried out by three-dimensional culture without causing an excess of cell aggregation and without requiring time and effort for medium replacement.

REFERENCE SIGNS LIST

A: cell culturing apparatus, B: cell culturing apparatus, 1: culture solution aspirator, 11: outer tube, 111: lumen, 112: air hole, 12: inner tube, 121: suction port, 13: filter, 2: suspension culture vessel, 3: culture solution supply channel, 4: air supply channel, 5: stirrer, 51: stirring bar, 6: culture solution aspirator, 61: outer tube, 611: lumen, 612: air hole, 62: inner tube, 621: suction port, 63: filter, 7: suspension culture vessel, 71: first region, 72: second region, 8: filter, 9: culture solution aspirator, 91: suction port

The invention claimed is:

1. A cell culturing apparatus comprising a culture solution aspirator having a double-tube structure comprising an outer tube and an inner tube inserted in a lumen of the outer tube, and a suspension culture vessel, wherein
in the culture solution aspirator,
the outer tube comprises a filter through which a culture solution is passed, and an air hole is positioned on the outer tube such that the air hole is not immersed in the culture solution to which communicate the lumen of the outer tube with the outside to allow negative pressure in the lumen of the outer tube to escape to the outside, and
the inner tube comprises a suction port for the culture solution passed through the filter.

2. The cell culturing apparatus according to claim 1, further comprising a culture solution supply channel which supplies a culture solution to the suspension culture vessel.

3. A culture solution aspirator having a double-tube structure comprising an outer tube and an inner tube inserted in a lumen of the outer tube, wherein
the outer tube comprises a filter through which a culture solution is passed, and an air hole is positioned on the outer tube such that the air hole is not immersed in the culture solution to which communicate the lumen of the outer tube with the outside to allow negative pressure in the lumen of the outer tube to escape to the outside, and
the inner tube comprises a suction port for the culture solution passed through the filter.

4. A cell culturing method in a suspension culture vessel, comprising the step of
discharging a culture solution in the suspension culture vessel to the outside of the suspension culture vessel using a culture solution aspirator having a double-tube structure comprising an outer tube and an inner tube inserted in a lumen of the outer tube, wherein
in the culture solution aspirator,
the outer tube comprises a filter through which a culture solution is passed, and an air hole, which is positioned on the outer tube such that the air hole is not immersed in the culture solution to which communicate the lumen of the outer tube with the outside to allow negative pressure in the lumen of the outer tube to escape to the outside, and
the inner tube comprises a suction port for the culture solution passed through the filter.

5. The cell culturing method according to claim 4, wherein the step is performed concurrently with the supply of a culture solution to the suspension culture vessel.

* * * * *

UNITED STATES PATENT AND TRADEMARK OFFICE
CERTIFICATE OF CORRECTION

PATENT NO. : 11,624,049 B2
APPLICATION NO. : 16/954889
DATED : April 11, 2023
INVENTOR(S) : Yamaura et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 135 days.

Signed and Sealed this
Seventh Day of January, 2025

Derrick Brent
*Acting Director of the United States Patent and Trademark Office*